United States Patent
Han et al.

(10) Patent No.: US 9,701,953 B2
(45) Date of Patent: *Jul. 11, 2017

(54) POLYNUCLEOTIDE ENCODING PSICOSE EPIMERASE AND METHOD OF PRODUCING PSICOSE USING THE SAME

(71) Applicant: SAMYANG CORPORATION, Seoul (KR)

(72) Inventors: Eun Jin Han, Seoul (KR); Hye Jung Kim, Daejeon (KR); Sin Hye Ahn, Goyang (KR); Se-Hui Jeon, Daegu (KR); Chong Jin Park, Daejeon (KR); Kang Pyo Lee, Seoul (KR)

(73) Assignee: SAMYANG CORPORATION, Seoul (KR)

( * ) Notice: Subject to any disclaimer, the term of this patent is extended or adjusted under 35 U.S.C. 154(b) by 0 days.

This patent is subject to a terminal disclaimer.

(21) Appl. No.: 15/101,459

(22) PCT Filed: Jul. 4, 2014

(86) PCT No.: PCT/KR2014/006023
§ 371 (c)(1),
(2) Date: Jun. 3, 2016

(87) PCT Pub. No.: WO2015/099256
PCT Pub. Date: Jul. 2, 2015

(65) Prior Publication Data
US 2016/0304853 A1  Oct. 20, 2016

(30) Foreign Application Priority Data

Dec. 26, 2013  (KR) ........................ 10-2013-0164686

(51) Int. Cl.
*C12N 9/90* (2006.01)
*C12P 19/02* (2006.01)
*C12P 19/24* (2006.01)

(52) U.S. Cl.
CPC ................ *C12N 9/90* (2013.01); *C12P 19/02* (2013.01); *C12P 19/24* (2013.01); *C12Y 501/03* (2013.01)

(58) Field of Classification Search
None
See application file for complete search history.

(56) References Cited

U.S. PATENT DOCUMENTS

2010/0190225 A1  7/2010  Oh

FOREIGN PATENT DOCUMENTS

| KR | 10-1106253 | 1/2012 |
| KR | 10-1203856 | 11/2012 |
| KR | 10-1318422 | 10/2013 |

OTHER PUBLICATIONS

Zhang, W. et al., 'Characterization of a novel metal-dependent D-psicose 3-epimerase from Clostridium scindens 35704', PLoS One, Apr. 30, 2013, vol. 8, Iss. 4, pp. 1-8 (e62987).
Kim, H. J. et al., 'Characterization of an Agrobacterium tumefaciens D-psicose 3-epimerase that converts D-fructose to D-psicose', Appl. Environ. Microbiol., Feb. 2006, vol. 72, No. 2, pp. 981-985.
Matsuo, T., Y. Baba, M. Hashiguchi, K. Takeshita, K. Izumori, and H. Suzuki., "Dietary D-psicose, a C-3 epimer of D-fructose, suppresses the activity of hepatic lipogenic enzymes in rats", Asia Pac. J. Clin. Nutr., vol. 10., Issue 3, pp. 233-237, Jan. 2001.
Matsuo, T., and K. Izumori., "D-Psicose, a rare sugar that provides no energy and additionally beneficial effects for clinical nutrition", Asia Pac. J. Clin. Nutr., vol. 13, p. S127, Jun. 2004.

*Primary Examiner* — Sheridan Swope
(74) *Attorney, Agent, or Firm* — Lex IP Meister, PLLC (57) ABSTRACT

A psicose 3-epimerase, a polynucleotide encoding the enzyme, a recombinant vector carrying the polynucleotide, a recombinant cell harboring the recombinant vector, and use thereof are provided.

9 Claims, 7 Drawing Sheets

5' ->TGCAAGTCGAGCGCCCCGCAAGGGGAGCGGCAGACGGGTGAGTAACGCGT
GGGAATCTACCCTTTTCTACGGAATAACGCAGGGAAACTTGTGCTAATAC
CGTATACGCCCTTCGGGGGAAAGATTTATCGGGAAAGGATGAGCCCGCGT
TGGATTAGCTAGTTGGTGGGGTAAAGGCCTACCAAGGCGACGATCCATAG
CTGGTCTGAGAGGATGATCAGCCACATTGGGACTGAGACACGGCCCAAAC
TCCTACGGGAGGCAGCAGTGGGGAATATTGGACAATGGGCGCAAGCCTGA
TCCAGCCATGCCGCGTGAGTGATGAAGGCCCTAGGGTTGTAAAGCTCTTT
CACCGGTGAAGATAATGACGGTAACCGGAGAAGAAGCCCCGGCTAACTTC
GTGCCAGCAGCCGCGGTAATACGAAGGGGGCTAGCGTTGTTCGGAATTAC
TGGGCGTAAAGCGCACGTAGGCGGACATTTAAGTCAGGGGTGAAATCCCG
GGGCTCAACCCCGGAACTGCCTTTGATACTGGGTGTCTAGAGTATGGAAG
AGGTGAGTGGAATTCCGAGTGTAGAGGTGAAATTCGTAGATATTCGGAGG
AACACCAGTGGCGAAGGCGGCTCACTGGTCCATTACTGACGCTGAGGTGC
GAAAGCGTGGGGAGCAAACAGGATTAGATACCCTGGTAGTCCACGCCGTA
AACGATGAATGTTAGCCGTCGGGCAGTTTACTGTTCGGTGGCGCAGCTAA
CGCATTAAACATTCCGCCTGGGGAGTACGGTCGCAAGATTAAAACTCAAA
GGAATTGACGGGGGCCCGCACAAGCGGTGGAGCATGTGGTTTAATTCGAA
GCAACGCGCAGAACCTTACCAGCCCTTGACATCCCGATCGCGGATTACGG
AGACGTTTTCCTTCAGTTCGGCTGGATCGGAGACAGGTGCTGCATGGCTG
TCGTCAGCTCGTGTCGTGAGATGTTGGGTTAAGTCCCGCAACGAGCGCAA
CCCTCGCCCTTAGTTGCCAGCATTTAGTTGGGCACTCTAAGGGGACTGCC
GGTGATAAGCCGAGAGGAAGGTGGGGATGACGTCAAGTCCTCATGGCCCT
TACGGGCTGGGCTACACACGTGCTACAATGGTGGTGACAGTGGGCAGCGA
GACCGCGAGGTCGAGCTAATCTCCAAAAGCCATCTCAGTTCGGATTGCAC
TCTGCAACTCGAGTGCATGAAGTTGGAATCGCTAGTAATCGCAGATCAGC
ATGCTGCGGTGAATACGTTCCCGGGCCTTGTACACACCGCCCGTCACACC
ATGGGAGTTGGTTCTACCCGAAGGTAGTGCGCTA->3'

SEQUENCE LISTING

```
<160> NUMBER OF SEQ ID NOS: 9

<210> SEQ ID NO 1
<211> LENGTH: 282
<212> TYPE: PRT
<213> ORGANISM: Artificial Sequence
<220> FEATURE:
<223> OTHER INFORMATION: amino acid sequence of D-psicose 3-epimerase
      originated from Ensifer adhaerens

<400> SEQUENCE: 1

Met Gln Gly Phe Gly Val His Thr Ser Met Trp Thr Met Asn Trp Asp
 1               5                  10                  15

Arg Pro Gly Ala Glu Arg Ala Val Ala Ala Val Lys Tyr Ala Val
            20                  25                  30

Asp Phe Ile Glu Ile Pro Met Leu Asn Pro Pro Ala Val Asp Thr Ala
        35                  40                  45

His Thr Arg Ala Leu Leu Glu Lys Asn Lys Leu Arg Ala Val Cys Ser
    50                  55                  60

Leu Gly Leu Pro Glu Arg Ala Trp Ala Ser Val Arg Pro Asp Ala Ala
65                  70                  75                  80

Ile Glu His Leu Lys Val Ala Ile Asp Lys Thr Ala Asp Leu Gly Gly
                85                  90                  95

Glu Ala Leu Ser Gly Val Ile Tyr Gly Gly Ile Gly Glu Arg Thr Gly
            100                 105                 110
```

Val Pro Pro Thr Glu Ala Glu Tyr Asp Asn Ile Ala Arg Val Leu Gln
            115                 120                 125

Ala Ala Ala Lys His Ala Lys Thr Arg Gly Ile Glu Leu Gly Val Glu
        130                 135                 140

Ala Val Asn Arg Tyr Glu Asn His Leu Ile Asn Thr Gly Trp Gln Ala
145                 150                 155                 160

Val Asp Met Ile Lys Arg Val Gly Ala Asp Asn Val Phe Val His Leu
                165                 170                 175

Asp Thr Tyr His Met Asn Ile Glu Glu Lys Gly Ile Gly Thr Gly Ile
            180                 185                 190

Leu Asp Ala Arg Asp Phe Ile Lys Tyr Ile His Leu Ser Glu Ser Asp
        195                 200                 205

Arg Gly Thr Pro Gly Tyr Gly Asn Cys Ala Trp Asp Glu Ile Phe Ala
    210                 215                 220

Thr Leu Ala Ala Ile Gly Phe Lys Gly Gly Leu Ala Met Glu Ser Phe
225                 230                 235                 240

Ile Asn Met Pro Pro Glu Val Ala Tyr Gly Leu Ala Val Trp Arg Pro
                245                 250                 255

Val Ala Arg Asp Glu Glu Glu Val Met Gly Asn Gly Leu Pro Phe Leu
            260                 265                 270

Arg Asn Lys Ala Arg Gln Tyr Gly Leu Ile
        275                 280

<210> SEQ ID NO 2
<211> LENGTH: 849
<212> TYPE: DNA
<213> ORGANISM: Artificial Sequence
<220> FEATURE:
<223> OTHER INFORMATION: Nucleotide sequence of D-psicose 3-epimerase of
      SEQ ID NO. 1

<400> SEQUENCE: 2
atgcagggtt ttggcgtcca tacgagcatg tggaccatga attgggatcg ccccggtgcg    60
gagcgcgccg ttgcggcggc ggtaaaatac gccgtcgact tcatcgagat cccgatgctc   120
aatccgccgg cggttgatac tgcccatacc agggcgctgc tggagaaaaa caagctgcgc   180
gcggtctgct cgctcggcct gccggagcgc gcctgggcat ccgtccgacc cgatgccgcg   240
atcgagcatc tgaaggtggc gatcgacaag acggccgatc tcggcggcga ggcgctgtcc   300
ggcgtcatct acggcggcat cggcgagcgc accggcgtgc cgccgactga agccgaatac   360
gacaacattg cccgtgtgct gcaggccgcc gccaagcacg ccaaaacccg cggcatcgaa   420
ctgggtgtcg aggcggtcaa ccgctacgag aaccacctga tcaacaccgg ttggcaagcg   480
gtcgacatga tcaagcgggt gggcgccgac aatgtcttcg tgcatctcga tacctaccac   540
atgaacatcg aggaaaaggg catcggcacc ggcatcctcg atgcacgcga cttcatcaaa   600
tacatccacc tgtccgaaag cgaccgcggc acgcccggct atggcaattg cgcctgggac   660
gagatcttcg cgacgctggc cgcgatcggt ttcaagggtg gctggcgat ggaaagcttc    720 atcaacatgc cgccggaagt ggcctatggc cttgcggtct ggcggccggt cgccagggac   780
gaagaggaag tgatgggcaa cggcctgccg ttccttagga acaaggcccg gcaatacgga   840
ttgatctag                                                            849

<210> SEQ ID NO 3
<211> LENGTH: 15
<212> TYPE: DNA
<213> ORGANISM: Artificial Sequence -continued

```
<220> FEATURE:
<223> OTHER INFORMATION: promoter for gene of SEQ ID NO. 2 in Ensifer
      adhaerens

<400> SEQUENCE: 3
gtcgcgacga aattc                                                    15

<210> SEQ ID NO 4
<211> LENGTH: 20
<212> TYPE: DNA
<213> ORGANISM: Artificial Sequence
<220> FEATURE:
<223> OTHER INFORMATION: primer

<400> SEQUENCE: 4
acatgatcgg ctccaatctc                                               20

<210> SEQ ID NO 5
<211> LENGTH: 20
<212> TYPE: DNA
<213> ORGANISM: Artificial Sequence
<220> FEATURE:
<223> OTHER INFORMATION: primer

<400> SEQUENCE: 5
tatttgatga agtcgcgtgc                                               20

<210> SEQ ID NO 6
<211> LENGTH: 20
<212> TYPE: DNA
<213> ORGANISM: Artificial Sequence
<220> FEATURE:
<223> OTHER INFORMATION: primer

<400> SEQUENCE: 6
gcacgcgact tcatcaaata                                               20

<210> SEQ ID NO 7
<211> LENGTH: 19
<212> TYPE: DNA
<213> ORGANISM: Artificial Sequence
<220> FEATURE:
<223> OTHER INFORMATION: primer

<400> SEQUENCE: 7
ggccgagata ccagcgcgc                                                19

<210> SEQ ID NO 8
<211> LENGTH: 29
<212> TYPE: DNA
<213> ORGANISM: Artificial Sequence
<220> FEATURE:
<223> OTHER INFORMATION: primer

<400> SEQUENCE: 8
agatatacat atgcagggtt ttggcgtcc                                     29

<210> SEQ ID NO 9
<211> LENGTH: 30
<212> TYPE: DNA
<213> ORGANISM: Artificial Sequence
```

-continued

```
<220> FEATURE:
<223> OTHER INFORMATION: primer

<400> SEQUENCE: 9
aaggctcgag gatcaatccg tattgccggg                                    30
```

POLYNUCLEOTIDE ENCODING PSICOSE EPIMERASE AND METHOD OF PRODUCING PSICOSE USING THE SAME

TECHNICAL FIELD

The present disclosure relates to a psicose 3-epimerase, a polynucleotide encoding the psicose 3-epimerase, a recombinant vector carrying the polynucleotide, a recombinant cell harboring the recombinant vector, and a use thereof in the production of psicose.

BACKGROUND ART

Psicose is a C-3 epimer of D-fructose which is 70% as sweet as D-fructose. Unlike D-fructose, psicose is largely unmetabolized in the body, and thus finds application as a sugar ingredient of various functional foods for use in blood sugar control, dental cavity prevention, and hepatic lipogenesis inhibition.

Sugar alcohols, widely used as alternatives to sugar, have the side effect of causing diarrhea upon uptake of a certain amount or more whereas no side effects are known for psicose.

Hence, psicose has attracted intensive interest to the use thereof as a sweetener, but since psicose is rarely found in nature, its effective production is a premise for application to the food industry.

Conventionally, psicose is chemically produced from D-fructose through the catalysis of molybdic acid ions. In the meantime, a biological method using a psicose epimerase from *Agrobacterium tumefaciens* has recently been known as one of the most efficient approaches. The chemical method suffers from the disadvantage of producing only a very small amount of psicose during molasses treatment or glucose isomerization, the process is expensive, and it generates by-products. Also, the biological method is disadvantageous in that the production is of high cost and is low in yield.

Therefore, there is a need for a method by which psicose can be produced at a temperature and pH condition suited for industrialization, with high yields and no by-product generation.

DISCLOSURE

Technical Problem

An embodiment provides an amino acid sequence of an enzyme capable of converting D-fructose to psicose.

Another embodiment provides a polynucleotide encoding the enzyme.

A further embodiment provides a recombinant vector carrying the polynucleotide.

A still further embodiment provides a recombinant cell harboring the recombinant vector.

Still another embodiment provides a composition for the production of psicose, comprising at least one selected from the group consisting of the enzyme, a polynucleotide encoding the enzyme, a recombinant vector carrying the polynucleotide, and a recombinant cell harboring the recombinant vector.

Yet another embodiment provides a method of producing psicose, using at least one selected from the group consisting of the enzyme, a polynucleotide encoding the enzyme, a recombinant vector carrying the polynucleotide, and a recombinant cell harboring the recombinant vector.

Technical Solution

A novel *Ensifer adhaerens* strain having high activity of converting D-fructose to psicose is isolated and identified from soil (*Ensifer adhaerens* SYG29; Accession No: KCCM11405P). An analysis on the total genes of the *Ensifer adhaerens* strain first revealed a polynucleotide encoding an enzyme responsible for the conversion of D-fructose to psicose, and its nucleotide sequence.

In addition, the polynucleotide is inserted to a recombinant vector and expressed to afford the enzyme having the activity of producing psicose from D-fructose, to complete the present invention.

That is, in the present invention, the amino acid sequence of a protein of which function is unknown and the nucleotide sequence of a gene encoding the protein are identified, and the protein is suggested as a D-psicose 3-epimerase which is capable of producing psicose at high yield. Therefore, an aspect of the present invention relates to a use of the gene and the protein in producing psicose, and a use of the protein as D-psicose 3-epimerase.

An embodiment provides a protein including or consisting essentially of the amino acid sequence set forth in SEQ ID NO: 1. The protein may have the activity of converting D-fructose to psicose. Hence, another embodiment provides a psicose epimerase which includes or consists essentially of the amino acid sequence set forth in SEQ ID NO: 1 and has the activity of converting D-fructose to psicose. The enzyme may have D-psicose 3-epimeration activity. For example, the protein or the enzyme may be obtained (derived) from *Ensifer adhaerens*, but is not limited thereto.

The protein or the enzyme may have the amino acid sequence set forth in SEQ ID NO: 1, but the amino acid sequence may be mutated by substitution, insertion and/or deletion so long as it retains the activity of converting D-fructose to psicose (e.g., D-psicose 3-epimeration activity). For example, the protein or the enzyme may include the amino acid sequence having a homology of 70% or more, 80% or more, 90% or more, 95% or more, 98% or more, or 99% or more with the amino acid sequence of SEQ ID NO: 1, with the retention of the activity of converting D-fructose to psicose.

The protein or the enzyme which has the amino acid sequence set forth in or sharing a homology of at least 70% with SEQ ID NO: 1 may range in molecular weight from 27 to 33 kDa, e.g., 29 to 31 kDa, as measured by sodium dodecyl sulfate polyacrylamide gel electrophoresis (SDS-PAGE).

In accordance with a further aspect thereof, the present invention provides a polynucleotide encoding the protein including or consisting essentially of the amino acid sequence of SEQ ID NO: 1. Also, a still further aspect of the present invention addresses a recombinant vector including (carrying) the polynucleotide encoding the protein. Still another aspect of the present invention provides a recombinant cell that harbors (includes) the recombinant vector, i.e., a cell that is transformed with the recombinant vector. Thus, the recombinant cell may express the protein.

The polynucleotide encoding the protein may include or consist essentially of the nucleotide sequence set forth in SEQ ID NO: 2 or a nucleotide sequence having substantial identity to SEQ ID NO: 2. As used herein, the term "substantial identity" means that a polynucleotide comprises a sequence that has at least 70% sequence identity, at least 80%, at least 90%, at least 95%, at least 98%, or at least 99% or 100%, compared to a reference sequence, as analyzed by a alignment program, and that a protein encoded by the polynucleotide sequence retains the activity of converting D-fructose to psicose.

A person having ordinary skill in the art will readily recognize that a polynucleotide of substantial identity that encodes an enzyme protein having the same activity as the reference enzyme can be prepared by substituting, adding or deleting one or more nucleotides by means of genetic engineering technology well known in the art. Identity comparison between two or more sequences may be calculated and expressed as percentages (%) using a computer program known in the art.

The polynucleotide may be used as itself alone or as being carried by a recombinant vector. The term "recombinant vector" refers to a recombinant nucleic acid molecule that can deliver an operatively linked polynucleotide of interest. The polynucleotide of interest may be operatively linked to at least one transcription regulatory element selected from among a promoter and a transcription termination factor. Also, the polynucleotide may be operatively linked to, for example, a chemical compound inducible element or a temperature sensitive element. The chemical compound inducible element may be selected from the group consisting of a lac operon, a T7 promoter, and a trc promoter. The T7 promoter, which is derived from T7 phage, contains a T7 terminator, as well.

The recombinant vector may be constructed as a vector for cloning or expression, using a method well known in the art. Any vector that is suitable for use in genetic recombination may be employed as the recombinant vector. For instance, it may be selected from the group consisting of, but not limited to, a plasmid expression vector, a viral expression vector (e.g., replication-defective retrovirus, adenovirus, adeno-related virus), and a viral vector having the same function. In detail, the recombinant vector may be suitable for expression in *E. coli*, and may be constructed on the basis of one selected from the group consisting of pET, pBR, pTrc, pLex, and pUC.

So long as it has an expression system that allows for the expression (overexpression) of the protein, any microorganism may be used as a host cell into which the recombinant vector is transformed. For example, *E. coli* may be useful. Examples of *E. coli* include, but are not limited to, BL21, JM109, K-12, LE392, RR1, DH5α and W3110, with preference for BL21(DE3). Also, the host cell may be selectable from among enteric bacteria and strains including *Bacillus* spp., such as *Bacillus subtilis* and *Bacillus thuringiensis*, *Corynebacteria* spp., such as *Corynebacterium glutamicum*, *Salmonella* spp., such as *Salmonella typhimurium*, *Serratia marcescens*, and various *Pseudomonas* spp.

As for the transformation of the recombinant vector into a host cell, it may be achieved by any method well known in the art. For example, illustrative, non-limiting examples of the method include protoplast fusion, electroporation, projectile bombardment, and infection with a viral vector.

As described above, the protein including or consisting essentially of the amino acid sequence of SEQ ID NO: 1 is an enzymatic protein with high activity of converting D-fructose to psicose. Thus, the protein including or consisting essentially of the amino acid sequence of SEQ ID NO: 1 or a recombinant cell expressing the protein may be usefully applied to the production of psicose.

In accordance with yet another aspect thereof, the present invention addresses a composition for the production of psicose, comprising at least one selected from the group consisting of a protein including or consisting essentially of the amino acid sequence of SEQ ID NO: 1, a polynucleotide encoding the protein, a recombinant vector carrying the polynucleotide, a recombinant cell harboring the recombinant vector, a culture of the recombinant cell, and a lysate of the recombinant cell. The composition for the production of psicose may be configured to produce psicose from D-fructose serving as a base. Containing an enzyme protein produced from the recombinant cell, the culture may include the recombinant cell, or may alternatively be in a cell-free form. The lysate may result from the lysis of the recombinant cell or may include a supernatant obtained by centrifuging the lysate, so that it contains the enzymatic protein produced from the recombinant cell in n either case. Unless stated otherwise herein, the recombinant cell means at least one selected from the group consisting of a cell mass of the strain, a culture of the strain and a lysate of the strain.

In accordance with a yet further aspect thereof, the present invention addresses a method for producing psicose, using at least one selected from a protein including or consisting essentially of the amino acid sequence of SEQ ID NO: 1, a polynucleotide coding for the protein, a recombinant vector carrying the polynucleotide, a recombinant cell harboring the recombinant vector, a culture of the recombinant cell, a lysate of the recombinant cell (hereinafter collectively referred to as "the enzymatic proteins"). The psicose-producing method comprises the reaction of the enzymatic proteins with D-fructose. In one embodiment, the reaction between the enzymatic proteins and D-fructose may be carried out by contacting the enzymatic proteins with D-fructose. In another embodiment, the contact between the enzymatic proteins and D-fructose may be carried out by, for example, mixing the enzymatic proteins with D-fructose or bringing D-fructose into contact with the enzymatic proteins immobilized to a support. In a further embodiment, the reaction between the enzymatic proteins and D-fructose may be carried out by culturing a cell mass of the recombinant cell in a medium containing D-fructose. The reaction of the enzymatic proteins with D-fructose leads to conversion and thus production of psicose from D-fructose.

In the psicose-producing method, efficiency may be brought in the production of psicose when the enzymatic proteins are used at a concentration of 0.001 mg/ml to 2.0 mg/ml in the reaction mixture, at a concentration of 0.003 mg/ml to 2.0 mg/ml, at a concentration of 0.003 mg/ml to 1.0 mg/ml, at a concentration of 0.01 mg/ml to 2.0 mg/ml, or at a concentration of 0.01 mg/ml to 1.0 mg/ml. When the enzymatic proteins are used at a concentration lower than the lower limit, the conversion yield of psicose may be poor. On the other hand, too high a concentration of the enzymatic proteins decreases the industrial economy of psicose production.

For effective production of psicose in the method, D-fructose, serving as a substrate, is used at a concentration of 40 to 80% (w/v) in the reaction mixture, for example, at a concentration of 55 to 75% (w/v). A concentration lower than the lower limit of D-fructose may decrease the economic feasibility of psicose in this manner. On the other hand, if present at a concentration higher than the upper limit, D-fructose is less apt to dissolve. Hence, the concentration preferably falls within the range. D-fructose may be in the form of a solution in a buffer or water (e.g., distilled water).

At higher pH values, the enzymatic proteins are more active. They retain 90% or higher activity at a pH of about or higher than 7, or at a pH of about or higher than 7.5, for example, at a pH of 7.5 to 10 (see FIG. 5). When account is taken of this optimal condition for the enzymatic proteins, the reaction may be carried out at a pH of 7 or higher, or at a pH of 7.5 or higher, for example, at a pH of 7 to 11, at a pH of 7 to 10, at a pH of 7 to 9, at a pH of 7.5 to 11, at a pH of 7.5 to 10, or at a pH of 7.5 to 9. In addition, the reaction may be conducted at a temperature of 30° C. or higher, for example, at a temperature of 40° C. or higher. However, the substrate D-fructose may be apt to undergo browning at 70° C. or higher. Hence, the reaction may be conducted under the temperature condition of from 40 to 70° C., for example, from 42 to 65° C., from 45 to 62° C., from 50 to 60° C., or from 52 to 57° C. In addition, a longer period of reaction time leads to a higher conversion rate of psicose. It is recommended to conduct the reaction for 1 hr or longer, for example, 2 hrs or longer, 3 hrs or longer, 4 hrs or longer, 5 hrs or longer, or 6 hrs or longer. However, the reaction time is preferably set forth within 48 hrs since when the reaction time is extended over 48 hrs, the increment of the conversion rate of psicose becomes slight, or may be decreased. Hence, the reaction time may be set forth to range from 1 to 48 hrs, from 2 to 48 hrs, from 3 to 48 hrs, from 4 to 48 hrs, from 5 to 48 hrs, or from 6 to 48 hrs. In consideration of industrial and economic aspects, the reaction time may fall within the range of 1 to 48 hrs, 2 to 36 hrs, 3 to 24 hrs, 3 to 12 hrs, or 3 to 6 hrs, but is not be limited thereto. This condition is selected in order to maximize the conversion yield from D-fructose to psicose.

In addition, when the recombinant cell is used in the psicose-producing method, its concentration may be set forth to range from 5 mg(dcw: dry cell weight)/ml or higher in the entire reaction mixture, for example, range from 5 to 100 mg(dcw)/ml, from 10 to 90 mg(dcw)/ml, from 20 to 80 mg(dcw)/ml, from 30 to 70 mg(dcw)/ml, from 40 to 60 mg(dcw)/ml, or from 45 to 55 mg(dcw)/ml. If the concentration of cell mass is below the lower limit, poor or almost no conversion activity of psicose is exhibited. On the other hand, a concentration exceeding the upper limit means crowding of cells which are likely to act as an obstructer to the optimization of the entire conversion yield of psicose.

The enzymatic protein having psicose conversion activity may show the property of a metalloenzyme the activity of which is controlled by metal ions. Hence, the presence of a metal ion may promote the reaction catalyzed by the enzymatic protein, thus increasing the production yield of psicose. The metal ion which can contribute to an improvement in the production yield of psicose may be selected from the group consisting of a copper ion, a manganese ion, a calcium ion, a magnesium ion, a zinc ion, a nickel ion, a cobalt ion, an iron ion, an aluminum ion, and any combination thereof. For example, either or both of a manganese ion and a magnesium ion may be used. When the amount of the metal ion is below 0.1 mM, there is only a slight effect on an improvement in the production yield of psicose. Thus, the metal ion is used in an amount of 0.1 mM or greater. On the other hand, when the amount of the metal ion exceeds 5 mM, the effect of addition is insignificant compared to the surplus amount. So, the amount of the metal ion is set forth to be 5 mM or less. For example, the metal ion is used in an amount of 0.1 mM to 5 mM, e.g., 0.1 to 2 mM, or 0.5 to 1.5 mM.

Therefore, the composition for the production of psicose may further comprise a metal ion whose kind and amount are as described above. Likewise, the method for producing psicose may further comprise adding a metal ion whose kind and amount are as described above. In one embodiment, the metal ion may be added to the substrate D-fructose or a mixture of D-fructose and the enzymatic proteins. In another embodiment, the metal ion may be added to a support to which the enzymatic proteins are immobilized (before the addition of D-fructose) or to a mixture of an enzymatic protein-immobilized support and D-fructose (after the addition of D-fructose), or may be added in mixture with D-fructose or individually together with D-fructose. When used, the recombinant cell may be cultured in a culture medium subsequent to, ahead of or simultaneously with the addition of the metal ion to the medium.

So long as it establishes an environment for maintaining the activity of the strain or the enzymatic protein produced from the strain for a long period of time, any support configured to immobilize the strain or the enzymatic protein thereto may be used. For example, sodium alginate may serve as the support. Sodium alginate, a naturally occurring colloidal polysaccharide abundantly found in the cell walls of brown algae, consists of β-D-mannuronic acid and α-L-gluronic acid, with a covalent β 1-4 linkage therebetween. Allowing for the stable immobilization of the strain or the enzyme thereto, the linear polymer may be advantageous for the production yield of psicose. In one embodiment, a 1.5~4.0% (w/v) sodium alginate solution (e.g., aqueous sodium alginate solution), for example, an about 2.5% (w/v) sodium alginate solution may be used for immobilizing the strain. By way of example, a cell mass of the strain, a culture broth containing the enzyme produced by the strain, or a lysate of the strain is mixed with 1 to 2 volumes of an aqueous sodium alginate solution, and the mixture is dripped to a 0.2 M calcium ion solution using a syringe pump and a vacuum pump, to form beads to which the cell mass of the strain, the culture containing the enzyme produced by the strain, or the lysate of the strain are immobilized. The enzyme may be purified from the strain, a culture of the strain or a lysate of the strain using a typical method, for instance, dialysis, precipitation, adsorption, electrophoresis, affinity chromatography, or ion exchange chromatography.

An embodiment provide a method for producing psicose, comprising reacting (or contacting) at least one selected from the group consisting of a protein comprising the amino acid sequence of SEQ ID NO: 1, a polynucleotide encoding the protein, a recombinant vector carrying the polynucleotide, a recombinant cell harboring the recombinant vector, a culture of the recombinant cell, and a lysate of the recombinant cell, with D-fructose.

In one embodiment, the method for producing psicose may comprise preparing and purifying a psicose epimerase protein including the amino acid sequence set forth in SEQ ID NO: 1, or an amino acid sequence sharing a homology of 70% or higher with the amino acid sequence of SEQ ID NO: 1; and reacting (or contacting) the protein with D-fructose.

In one embodiment, the method for producing psicose may comprise culturing and recovering a recombinant cell which expresses a protein including or consisting essentially of the amino acid sequence set forth in SEQ ID NO: 1; and reacting (or contacting) the recombinant cell or the enzymatic protein isolated from the recombinant cell with D-fructose.

The culturing of the recombinant cell may be conducted under a medium and condition readily selected according to the property of the strain (host cell) by those skilled in the art. For example, the culturing may be a continuous-type culture, a semi-continuous-type culture, or a batch-type culture, but is not limited thereto. The medium contains a solution and a solid, a semi-solid or rigid support for supporting host cells, such as *E. coli*, or cellular contents, and may be selected from the group consisting of standard 2YT, LB, SOB and TB media.

Generally, the culture of the recombinant cell may be obtained under a condition suitable to culture host cells (e.g., E. coli). For example, the recombinant cell may be cultured at 35° C. to 37° C. with stirring at 150 to 250 rpm. In order to induce the overexpression of the enzymatic protein, an inducer, such as that typically used in the art, may be added. By way of example, when the inducible element is a lac operon or a trc promoter, lactose or IPTG (isopropyl β-D-1-thiogalactopyranoside) may be used as an inducer. The time of induction may be suitably determined by those of ordinary skill in the art.

The recombinant cell may be isolated from the culture by centrifugation and/or filtration. The enzymatic protein may be concentrated in a supernatant obtained by homogenizing the strain and centrifuging the homogenate or may be obtained by fractionating the supernatant, and optionally by chromatographic purification of the fraction. For example, the recovered strain is suspended in 50 mM phosphate buffer, lyzed, and centrifuged. The supernatant is loaded to a Ni-NTA column (Qiagen), followed by eluting the enzymatic protein with 20 mM and 250 mM imidazole.

In the method, the reaction with D-fructose may be performed under a condition configured to optimize the activity of the enzymatic protein, for example, at a pH of 7 or higher, or at a pH of 7.5 or higher, e.g., at a pH of 7 to 11, 7 to 10, 7 to 9, 7.5 to 11, 7.5 to 10, or 7.5 to 9, and/or at a temperature of 40 to 70° C., e.g., 42 to 65° C., 45 to 62° C., 50 to 60° C., or 52 to 57° C. D-fructose may be used at a concentration of 40 to 75% (w/v), e.g., 50 to 75% (w/v) in the reaction mixture. Given D-fructose within the range, the method can produce psicose economically and effectively.

In addition, the recovered recombinant cell, if employed, is preferably washed two or more times with, for example, 0.85% (w/v) NaCl, ahead of reaction with D-fructose.

Further, the reaction with D-fructose may be performed in the presence of ions of at least one metal consisting of manganese and magnesium. The metal ions may be used at a concentration of 0.1 mM to 5 mM, for example, 0.1 to 2 mM, or 0.5 mM to 1.5 mM. A metal ion concentration less than the lower limit cannot bring about sufficient encouragement into the activity of the enzyme. When the metal ion is used at a concentration higher than the upper limit, the increment of the effect obtained is slight, compared to the amount used.

After being produced from D-fructose using the method of the present invention, psicose can be purified by a typical method which can be readily selected by a person skilled in the art, for example, from the group consisting of centrifugation, filtration, crystallization, ion exchange chromatography, and a combination.

Advantageous Effects

The novel psicose epimerase protein according to the present invention, which is an enzyme having the activity of producing psicose, is superior in thermal stability under an industrially applicable condition, has a long half life, and allows for the mass production of psicose from D-fructose at high yield. Therefore, the D-psicose 3-epimerase and the method for producing psicose using the same in accordance with the present invention are expected to find useful applications in various food, pharmaceutical and cosmetic industries.

MODE FOR INVENTION

A better understanding of the present invention may be obtained through the following examples which are set forth to illustrate, but are not to be construed as the limit of the present invention.

Example 1

Culturing of the Soil Bacterium *Ensifer adhaerens* with Activity of Converting D-Fructose to Psicose An *Ensifer adhaerens* strain (*Ensifer adhaerens* SYG29; Accession No: KCCM11405P) was cultured at 30° C. for 24 hrs in a minimal medium ($KH_2PO_4$ 2.4 g/L, $K_2HPO_4$ 5.6 g/L, $(NH_4)_2.SO_4$ 2.6 g/L, $MgSO_4.7H_2O$ 0.1 g/L, yeast extract 1 g/L) containing 1% psicose, with agitation. Centrifugation at 4,000 rpm for 20 min recovered a cell mass from the culture.

The strain is a psicose-producing strain which was selected as follows.

In 10 mL of 0.85% (w/v) NaCl was suspended 1 g of rhizosphere soil, and 100 ul (microliters) drawn from the suspension was spread over an agar plate and incubated at 30° C. Among the colonies formed on the agar plates, selection was made of those distinct in shape and size. The selected colonies were inoculated into a minimal medium ($KH_2PO_4$ 2.4 g/L, $K_2HPO_4$ 5.6 g/L, $(NH_4)_2$. $SO_4$ 2.6 g/L, $MgSO_4.7H_2O$ 0.1 g/L, yeast extract 1 g/L), and cultured at 30° C. for 24 hrs with agitation. Centrifugation recovered a cell mass. This cell mass was suspended in 100 μL of a 50 mM PIPES (piperazine-N,N'-bis(2-ethanesulfonic acid)) buffer (pH 8.0) and lyzed using an ultrasonic processor (ColepParmer). After centrifugation of the lysate at 12,000 rpm and 4° C. for 10 min, the supernatant thus formed was recovered and used as a crude enzyme. 10 mM Psicose was treated as a substrate at 30° C. for 8 hrs with the crude enzyme.

Conversion from psicose to D-fructose was monitored by thin layer chromatography (TLC) and high-performance liquid chromatography (HPLC). TLC analysis was performed using a 20 cm×5 cm silica gel (Silica gel 60 F254(Merck, Germany)) solid phase, with development with a mixture of 85:15 acetonitrile and water as a mobile phase for 3.5 min twice. For HPLC, Refractive Index Detector (Agilent 1260 RID) equipped with Aminex HPX-87C column (BIO-RAD) was used. Water served as a mobile solvent at a flow rate of 0.6 ml/min at 80° C.

Figure 10:
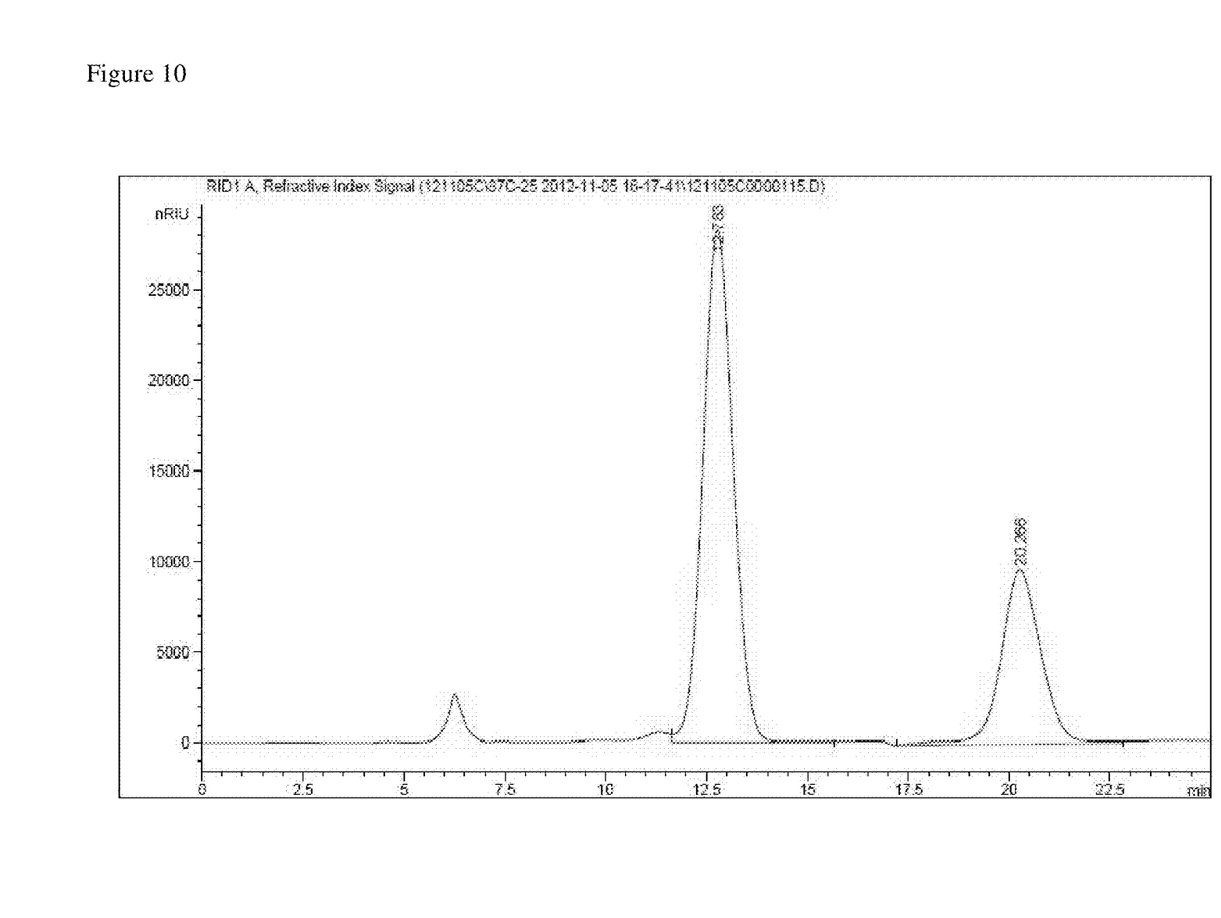
FIG. 10 is an HPLC chromatogram showing the activity of the strain of Example 1 to produce psicose from fructose of high concentration.

Strains which were found to convert psicose to D-fructose, as analyzed by TLC, were inoculated into a minimal medium containing 1% (w/v) fructose and 0.05% (w/v) psicose, and cultured at 30° C. for 24 hrs. Cell mass was recovered by centrifugation. The cell mass was washed with 0.85% (w/v) NaCl, and suspended at a concentration of 40 mg-dcw/ml in 50 mM PIPES buffer (pH 8.0) containing 400 g/L fructose and 1 mM manganese ions, and reacted with D-fructose at 70° C. for 6 hrs, followed by terminating the reaction by heating the reaction mixture at 100° C. for 5 min. HPLC analysis confirmed the production of psicose. For HPLC, Refractive Index Detector (Agilent 1260 RID) equipped with Aminex HPX-87C column (BIO-RAD) was used under the condition described above (solvent: water; temperature: 80° C.; flow rate: 0.6 ml/min). The results are given in FIG. 10. Final selection was made of the strain which was found to produce psicose in the greatest amount, as analyzed by HPLC analysis.

Figure 11:
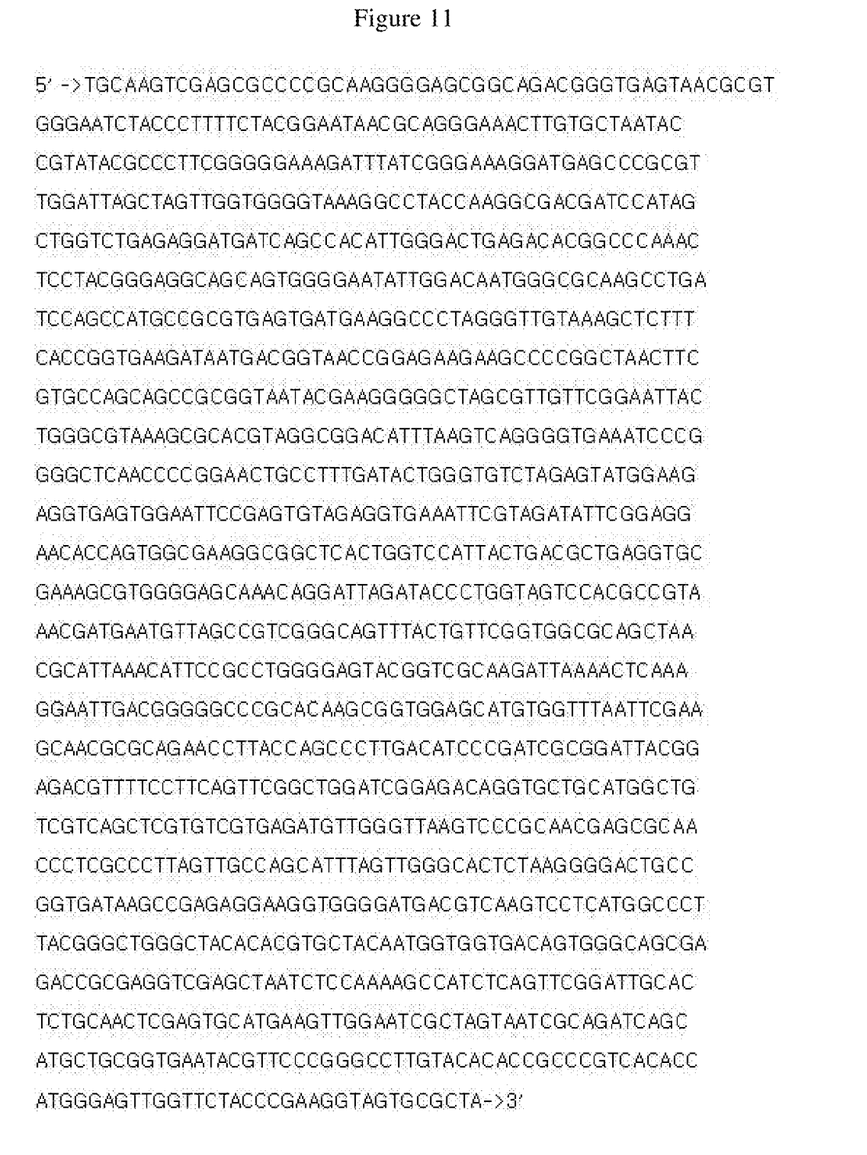
FIG. 11 shows the nucleotide sequence of 16S ribosomal RNA of the strain KCCM11405P (5'→3').

The strain was deposited in the Korean Culture Center of Microorganisms on Mar. 29, 2013, with accession No. KCCM11405P. The nucleotide sequence (5'→3') of 16S ribosomal RNA of the strain is shown in FIG. 11.

Example 2: Purification of Picose Epimerase Derived from *Ensifer adhaerens*

The cell mass recovered in Example 1 was suspended in 50 mM PIPES buffer (pH 7.0) containing 1 mM phenylmethylsulfonyl fluoride (PMSF), and lyzed at 4° C. for 40 min using an ultrasonic processor (Cole-Parmer). After centrifugation of the lysate at 13,000 rpm and 4° C. for 20 min, the supernatant was used as a crude enzyme.

Protein precipitation was made by adding 50-60% of saturated ammonium sulfate [(NH$_4$)$_2$.SO$_4$] to the crude enzyme, followed by centrifugation at 4° C. and 13,000 rpm for 20 min to recover the protein precipitate. Dialysis against 50 mM PIPES buffer (pH 7.0) for 12 hrs gave a partially purified enzyme.

After thermal treatment at 60° C. for 10 min, the partially purified enzyme was centrifuged at 4° C. and 8,000 rpm for 20 min. The supernatant was equilibrated with a 50 mM Tris-HCl buffer (pH 8.0), and subjected to Hi-trap Q ion exchange chromatography column (Amersham Biosciences, Uppsala, Sweden). The bound protein was eluted with a gradient of up to 1.0 M of NaCl. Thereafter, the fractions were measured for activity, and active fractions were pooled, and concentrated.

The sample separated by Hi-trap Q was equilibrated with a 10 mM sodium phosphate (pH 6.8) buffer, and then loaded to a Biogel hydroxyapatite column (Bio-Rad, Hercules, Calif., USA), followed by eluting with a concentration gradient of 10-100 mM sodium phosphate (pH 6.8). After a test for activity, active fractions were pooled and concentrated.

Again, the sample separated by the Biogel hydroxyapatite column was equilibrated with 50 mM sodium phosphate (pH 7.0) containing 1.5 M ammonium sulfate, adsorbed to a Hi-trap phenyl column (Amersham Biosciences, Uppsala, Sweden), and eluted with a gradient of 1.5-0 M ammonium sulfate.

From the *Ensifer adhearens* strain, the enzyme was purified according to the five-step procedure described above, and the results are summarized in Table 1.

Figure 1:
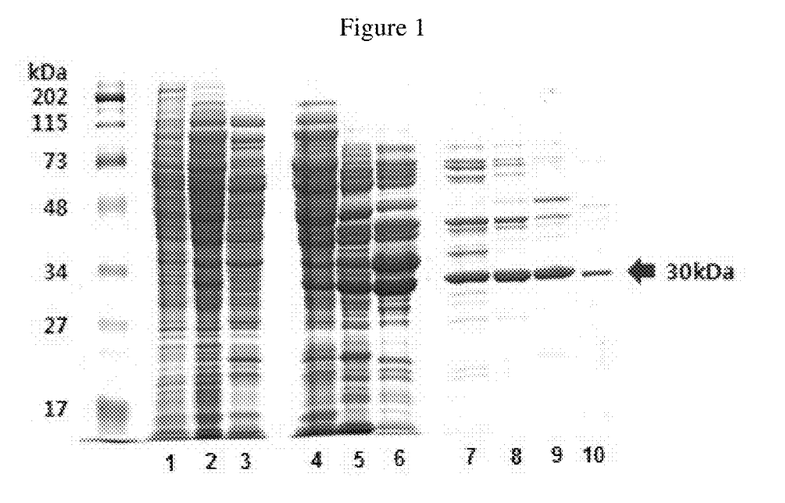
FIG. 1 is an image of SDS-PAGE illustrating the purification procedure according to one embodiment of the present invention (lane 1: crude enzyme, lane 2: ammonium sulfate, lane 3: thermal treatment, lane 4: Hi-trap Q, lanes 5 and 6: Hydroxyapatite, lanes 7, 8, 9 and 10: Hi-trap phenyl).

The degree of purification in each step was evaluated by SDS-PAGE. SDS-PAGE was performed on 12% polyacrylamide gel under an electric field of 20 mA. The result is shown in FIG. 1. As can be seen in FIG. 1, the purified protein of interest was read at a molecular weight of about 30 kDa (FIG. 1). After the purified protein with a concentration of 0.004 mg/ml was reacted with 50 mM D-fructose at 55° C. for 10 min, the resulting reaction mixture was analyzed by HPLC in the same manner as in Example 1. Data of the HPLC (the same condition as in Example 1) proved that the purified protein has the activity of producing psicose from D-fructose. Hence, the purified protein has the same activity as the D-psicose epimerase, which acts to convert D-fructose to psicose.

Example 3: Determination of N-Terminal Amino Acid Sequence of D-Psicose 3-Epimerase The purified protein was analyzed for N-terminal amino acid sequence in E-Mass. Co. The first 44 amino acid residues were revealed to have the sequence of MQGF-GVHTSMWTMNWDRPGAERAVAAAVKYAVDFIEIP-MLNPPA. This amino acid sequence was compared with the GenBank database (NCBI) using a BLAST program. A BLAST search showed that the purified protein shares a homology of about 80% with D-tagatose epimerase (accession number; YP002823363.1) of *Sinorhizobium* sp. (*Sinorhizobium fredii* NGR234).

Example 4: Gene Isolation of D-Psicose 3-Epimerase 4-1. Design of Synthetic Primers for Amplifying Gene of Interest To design DNA primers for use in amplifying a gene which encodes a protein with psicose converting activity, the following experiment was conducted. On the basis of the protein BLAST search (NCBI), enzymes (Accession Nos.: YP002823363.1, YP006398480.1, YP005192599.1, NP437010.1) that were found to have at least 80% homology with the N-terminal amino acid sequence of the *Ensifer adhaerens* psicose converting enzyme of Example 3, were selected. These enzymes were identified to have in common nucleotide sequences encoding sugar ABC transporter and carbohydrate kinase in regions proximal to 5' and 3' termini, respectively.

The full DNA sequences of genes encoding the entire D-psicose 3-epimerases were established using DNA fragments covering genes encoding the sugar ABC transporter and the carbohydrate kinase which are located in common at regions proximal to 5' and 3' termini of D-psicose 3-epimerase genes, respectively, wherein the genes encoding the sugar ABC transporter and the carbohydrate kinase were used merely as markers for obtaining the full DNA sequences.

Based on the genes, the following primers of SEQ ID NOS: 4, 5, 6 and 7 were synthesized for use in amplifying DNA coding for the protein with psicose converting enzyme activity.

SEQ ID NO: 4:
5' ACA TGA TCG GCT CCA ATC TC 3'

SEQ ID NO: 5:
5' TAT TTG ATG AAG TCG CGT GC 3'

SEQ ID NO: 6:
5' GCA CGC GAC TTC ATC AAA TA 3'

SEQ ID NO: 7:
5' GGC CGA GAT ACC AGC GCG C 3'

4-2. Acquisition of DNA Fragment Coding Partially for Psicose Converting Enzyme by PCR on Ensifer adhaerens-Derived Chromosomal DNA After being recovered by centrifugation from 5 ml of the cell culture prepared in Example 1, a cell mass was subjected to DNA extraction using a genomic DNA extraction kit (Bioneer Co.) according to the instruction provided by the manufacturer. A gene of interest was amplified by PCR using a pair of synthetic DNA primers of SEQ ID NOS: 4 and 5, or 6 and 7, with the chromosomal DNA from Ensifer adhaerens (Ensifer adhaerens SYG29; Accession No: KCCM11405P) serving as a template. PCR was performed in Thermal Cycler (Perkin Elmer. Co.), with 30 cycles of 94° C. for 1 min, 50° C. for 1 min, and 72° C. for 1 min. PCR products were detected at about 1 kb, as measured by agarose gel electrophoresis, after loading 2 µl to a 1 agarose gel.

Base sequencing of each DNA fragment identified a portion of the polynucleotide encoding the psicose converting enzyme. On the basis of the identified sequence, primers were designed to contain NdeI and XhoI (SEQ ID NO: 8: 5' AGA TAT ACA TAT GCA GGG TTT TGG CGT CC 3'; SEQ ID NO: 9: 5' AAG GCT CGA GGA TCA ATC CGT ATT GCC GGG 3'), and used for PCR on the chromosomal DNA of the Ensifer adhaerens strain. The PCR product was read at about 0.9 kb on 1 agarose gel by electrophoresis after loading 2 µl of the PCR mixture to the agarose gel. Its sequence is set forth in SEQ ID NO: 2.

Base sequencing analysis also detected a putative promoter sequence, as set forth in SEQ ID NO: 3.

4-3. Cloning of D-Psicose 3-Epimerase Gene

Figure 2:
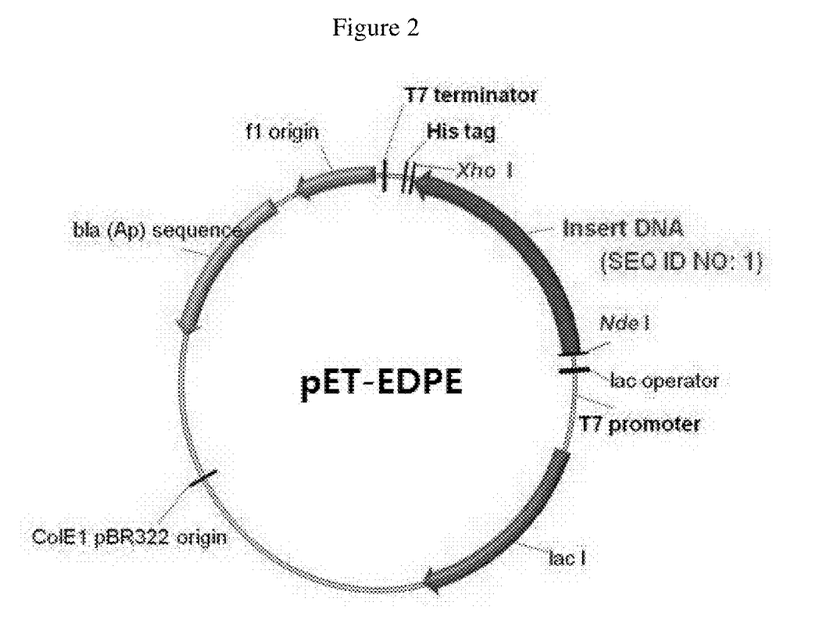
FIG. 2 is a cleavage map of a recombinant vector for expressing D-psicose 3-epimerase protein according to one embodiment of the present invention.

The polynucleotide (SEQ ID NO: 2) acquired by PCR was digested with NdeI and XhoI(NEB) before insertion into the same restriction site of the expression vector pET21a (Nobagen) to construct a new recombinant expression vector, designated pET21a/psicose 3-epimerase (pET-EDPE) (see FIG. 2). This recombinant vector was transformed into E. coli BL21 (DE3) (invitrogen) by heat shock (Sambrook and Russell: Molecular Cloning).

The transformant thus obtained was inoculated at a density of $10^4$ CFU/ml in 5 ml of LB-ampicillin media (Difco), after which incubation was conducted at 37° C. to an O.D.600 nm of 1.5 with shaking at 200 rpm. Then, the culturing was scaled up in 200 ml of LB-ampicillin broth in an incubator which was maintained at 37° C. and shook at 200 rpm. When the O. D. at 600 nm of the culture reached 0.5, the over-expression of the enzyme of interest was induced with 0.1 mM IPTG (isopropyl-β-D-thio-galactoside). From the time of induction, the cells were incubated at 16° C. for 16 hrs with shaking at 150 rpm.

Centrifugation at 4000 rpm for 20 min recovered a cell mass. This was washed twice with 0.85% (w/v) NaCl before use in enzyme purification.

Example 5: Purification and Characterization of D-Psicose 3-Epimerase 5-1. Purification of D-Psicose 3-Epimerase The cell mass recovered in Example 4-3 was suspended in a lysis buffer (50 mM Tris-HCl 300 mM NaCl pH 7.0, 10 mM imidazol), and lyzed at 4° C. for 20 min using an ultrasonic processor (ColepParmer). The lysate was centrifuged at 13000 rpm for 20 min, and the supernatant was loaded to a Ni-NTA column (Ni-NTA Superflow, Qiagen) pre-equilibrated with a lysis buffer, followed by sequentially eluting with 50 mM Tris-HCl/300 mM NaCl pH 7.0 containing 20 mM imidazole and 250 mM imidazole. The protein present in the final eluate obtained by fractioning with 50 mM Tris-HCl/300 mM NaCl pH 7.0 containing 250 mM imidazole was transferred to a buffer for measuring enzyme activity (50 mM PIPES pH 7.0).

5-2. Dependency of D-Psicose 3-Epimerase on Metal Ion

To examine the dependency of the D-psicose epimerase obtained in Example 5-1 on metal ions, its activity was measured in the presence of 1 mM $MgSO_4$ or $MnCl_2$.

With respect to the enzyme activity, one unit is defined as the amount of the enzyme that catalyzes the production of 1 micromole of psicose (per a minute) from D-fructose, when reacting with 50 mM fructose at 55° C. in the presence of the metal ions in 50 mM PIPES (piperazine-N,N'-bis(2-ethanesulfonic acid)) buffer (pH 7.0). For a control (Non), no metal ions were used.

The enzyme activity was calculated by dividing the amount of produced psicose (mM) by the amount of used enzyme and the reaction time. The amount of psicose was determined by HPLC. The HPLC analysis was performed using a 87C (BIO-RAD) column, with development with water 100% v/v) as a mobile phase at a flow rate of 0.6 ml/min at 80° C. Psicose was detected by Refractive Index Detector (Agilent 1260 TID).

Figure 3:
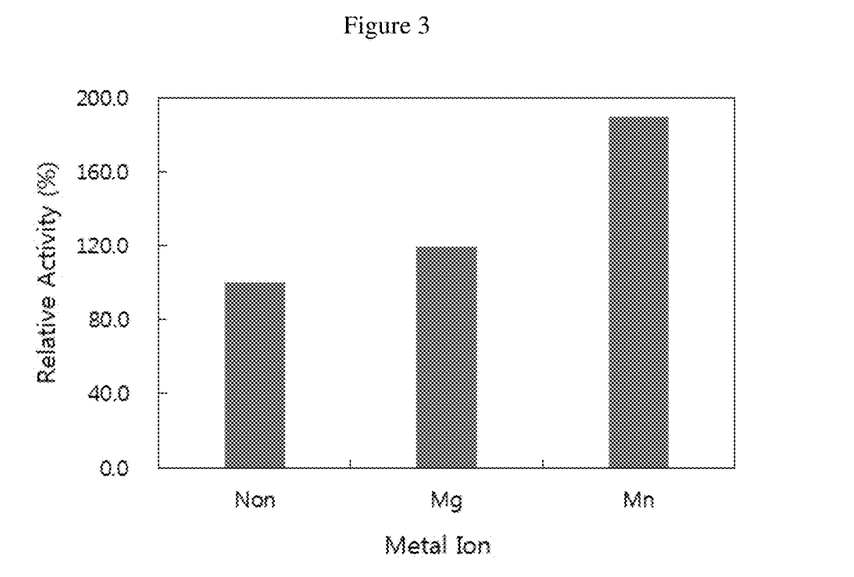
FIG. 3 is a graph showing the activity of the D-psicose 3-epimerase of one embodiment according to kind of metal ions used.

Enzyme activity measured in the presence of each metal ion was compared with that of the control, and the result is given in FIG. 3. As is apparent from the data of FIG. 3, the activity of the enzyme of Example 5-1 increases with manganese or magnesium ions, and thus is dependent on metal ions.

5-3. Effect of Temperature and pH on Activity of D-Psicose 3-Epimerase

An examination was made of the effect of pH and temperature on the activity of psicose 3-epimerase. In this regard, the enzyme was reacted with the substrate fructose at various pH values and temperatures.

Figure 4:
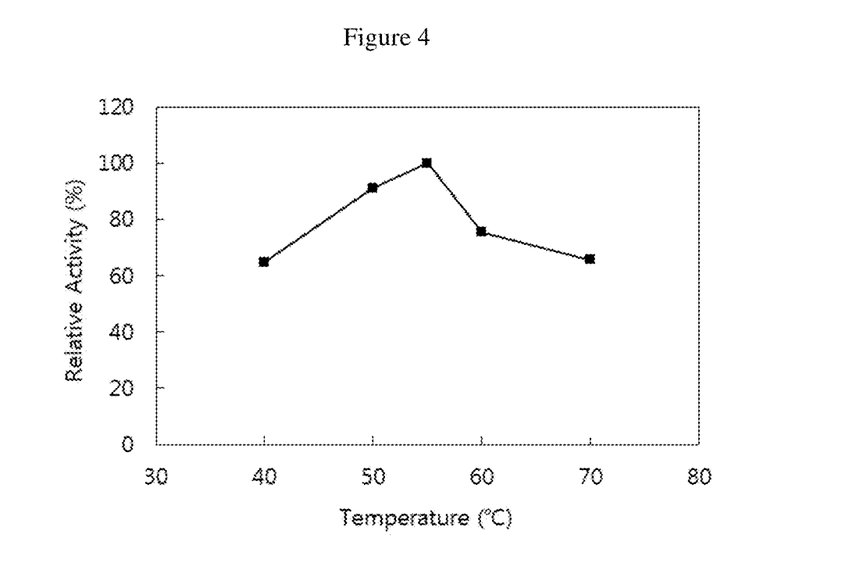
FIG. 4 is a graph showing the activity of D-psicose 3-epimerase of one embodiment according to temperature.

First, enzyme activity was measured at a pH of 7.0, with the reaction temperature varying from 40 to 70° C. Reference was made to the procedure of Example 5-2 with regard to the measurement of enzyme activity. The results are given FIG. 4. As can be seen in FIG. 4, the enzyme exhibited high conversion activity at a temperature range of 50 to 60° C., with a peak at 55° C. In FIG. 4, the relative activity on Y axis is expressed as percentage of the maximum activity of the control.

Figure 5:
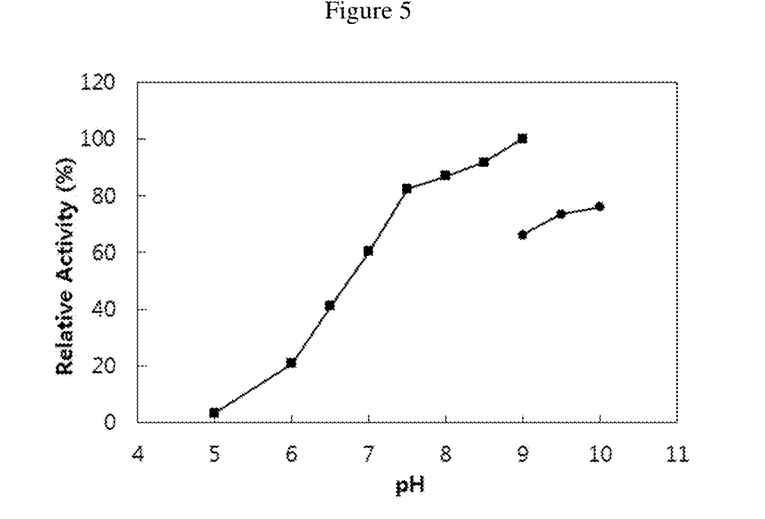
FIG. 5 is a graph showing the activity of D-psicose 3-epimerase of one embodiment according to pH (■: Mcilvaine buffer, ●: Glycine-NaOH buffer).

Also, in order to examine the effect of pH, enzyme activity was measured at 55° C. after reaction in Mcilvaine buffers with pH 5.0-9.0, or 50 mM Glycine-NaOH buffers with pH 9.0-10.0. The results are given in FIG. 5. As can be seen in FIG. 5, the enzyme became more active in more alkaline conditions, with the retention of 90% or higher activity at a pH of 7.5-10.0. In this regard, the activity was measured after 0.5 units/ml of the enzyme was reacted with 50 mM D-fructose for 10 min under the individual pH and temperature conditions set forth above, followed by heating at 100° C. for 5 min for reaction termination.

As is understood from the results, the psicose 3-epimerase according to the present invention does not fluctuate much in activity over a wide range of temperature and pH, which is advantageous for industrial applicability. Thus, the enzyme of the present invention is expected to have advantageous applications in the industrialization of psicose.

5-4. Assay for Thermal Stability of D-Psicose 3-Epimerase

To examine the stability of the psicose 3-epimerase to temperature changes, the enzyme purified in Example 5-1 was thermally treated at 55° C. and 60° C. for a predetermined period of time (8 hrs), and 0.5 units/ml of the thermally treated enzyme was reacted with 50 mM D-fructose at pH 7.0 and 55° C. for 10 min in a 50 mM PIPES buffer containing 1 mM $MnCl_2$. The reaction was terminated by heating at 100° C. for 5 min. Enzyme activities according to the time of thermal treatment were measured.

Figure 6:
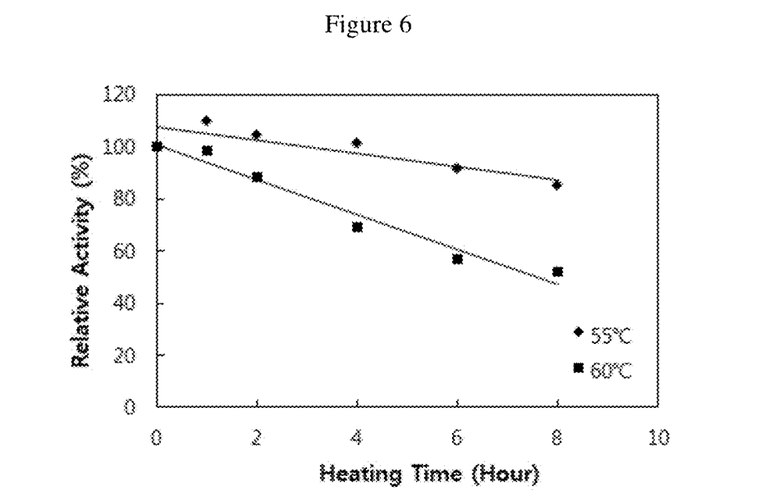
FIG. 6 is a graph showing the activity of D-psicose 3-epimerase of one embodiment at 55° C. and 60° C. according to time.

Results are given in FIG. 6. As can be seen in FIG. 6, the enzyme purified in Example 5-1 was calculated to have a half-life of about 22 hrs and 7 hrs at 55° C. and 60° C., respectively. These data are far higher than those of most psicose 3-epimerase enzymes previously reported, indicating that the psicose 3-epimerase of the present invention is superior in thermal stability to the temperatures at which the enzymatic reaction can be facilitated industrially.

5-5. Assay for Kinetic Parameter of D-Psicose 3-Epimerase

An examination was made of the reaction rate of the *Ensifer adhaerens*-derived psicose epimerase purified in Example 5-1. To this end, the enzyme was assayed for kinetic parameters.

A 50 mM PIPES buffer containing the enzyme at a concentration of 0.5 unit/ml and 1 mM $MnCl_2$ was incubated at pH 7.0 and 55° C., together with the substrate fructose whose concentration varied from 10 to 50 mM. The reaction was terminated by heating at 100° C. for 5 min.

Figure 7:
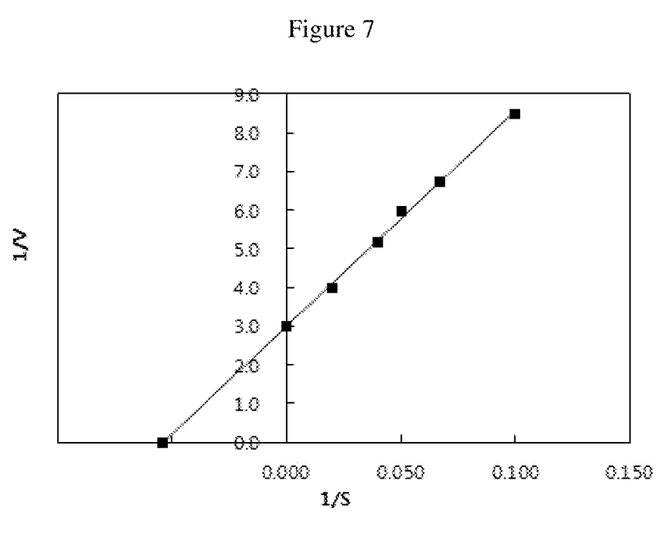
FIG. 7 is a double reciprocal (Lineweaver-Burk) plot of the D-psicose 3-epimerase of one embodiment.

The results are given in FIG. 7. In FIG. 7, the rate of the enzymatic reaction is described according to the Michaelis-Menten Equation where Km and $k_{cat}$ are calculated to be 18.6 mM and 2511.2 $min^{-1}$, respectively.

In addition, the psicose 3-epimerase according to the present invention was found to have a catalytic efficiency of 135 with regard to D-fructose, which is higher than 85, the catalytic efficiency of the conventional psicose 3-epimerase derived from *Agrobacterium tumefaciens*.

5-6. Production of Psicose of High Concentration from D-Fructose by D-Psicose 3-Epimerase To produce psicose at a high concentration, the D-psicose 3-epimerase of 0.1~0.5 mg/ml, purified in Example 5-1, was reacted with D-fructose of high concentration (400 g/L) at 55° C. in a 50 mM PIPES buffer, pH 7.0, containing 1 mM $MnCl_2$.

The psicose produced was quantitatively analyzed in the same manner as in Example 5-2 to determine the conversion rate from D-fructose to psicose. Since highly concentrated fructose was used, a sample taken at each time schedule was diluted 20 times before HPLC analysis.

Figure 8:
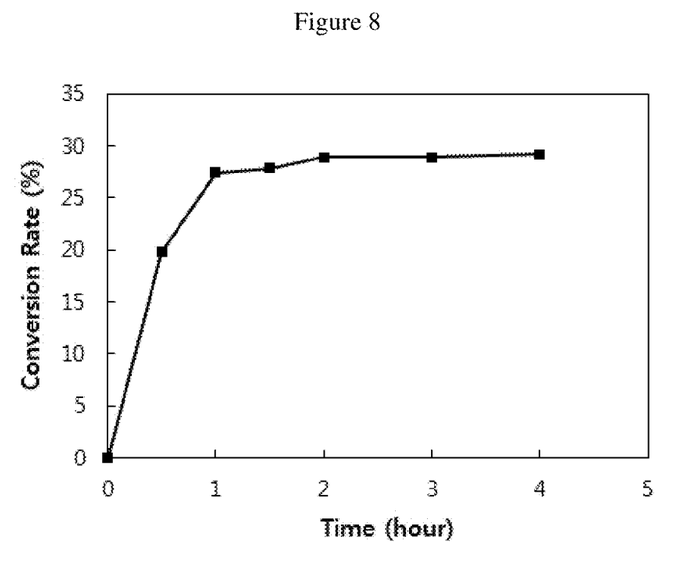
FIG. 8 is graph showing the production yield (conversion rate) of psicose from D-fructose of high concentration using the D-psicose 3-epimerase of one embodiment.

Results are given in FIG. 8. When the enzyme was used at a concentration of 0.5 mg/ml, as can be seen in FIG. 8, the production of psicose amounted to 118.6 g/L, with a psicose conversion rate of about 30%.

Figure 9:
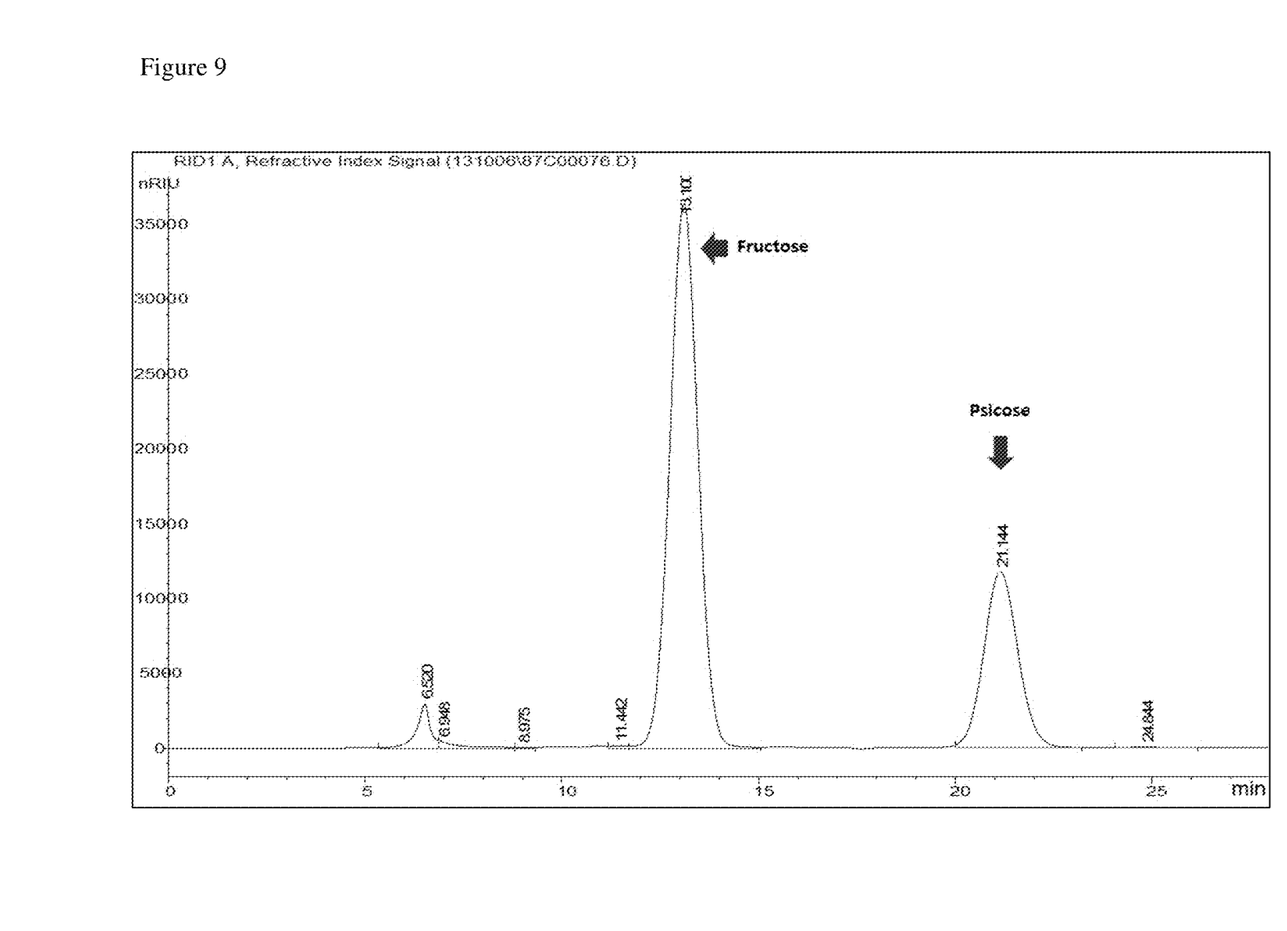
FIG. 9 is an HPLC chromatogram showing the activity of the D-psicose 3-epimerase of one embodiment to produce psicose from fructose of high concentration.

Meanwhile, psicose productivity by bioconversion from D-fructose of high concentration was measured by HPLC, and the results are given in FIG. 9.

[Accession No.]

Depository Authority: Korean Culture Center of Microorganisms

Accession No.: KCCM11405P

Deposition Date: 29 Mar. 2013

---

The invention claimed is:

1. A method for producing psicose, comprising reacting at least one selected from the group consisting of a protein comprising the amino acid sequence of SEQ ID NO: 1, a recombinant cell harboring a recombinant vector carrying a polynucleotide encoding the protein, a culture broth of the recombinant cell, and a lysate of the recombinant cell, with D-fructose.

2. The method of claim 1, wherein the D-fructose is used at a concentration of 55 to 75% (w/w).

3. The method of claim 1, wherein the reacting is carried out at a pH of 7 to 10.

4. The method of claim 1, wherein the reacting is carried out at a temperature of 40 to 70° C.

5. The method of claim 1, which further comprises adding at least one selected from the group consisting of a copper ion, a manganese ion, a magnesium ion, a zinc ion, a nickel ion, a cobalt ion, an iron ion, an aluminum ion, and a calcium ion.

6. The method of claim 2, which further comprises adding at least one selected from the group consisting of a copper ion, a manganese ion, a magnesium ion, a zinc ion, a nickel ion, a cobalt ion, an iron ion, an aluminum ion, and a calcium ion.

7. The method of claim 3, which further comprises adding at least one selected from the group consisting of a copper ion, a manganese ion, a magnesium ion, a zinc ion, a nickel ion, a cobalt ion, an iron ion, an aluminum ion, and a calcium ion.

8. The method of claim 4, which further comprises adding at least one selected from the group consisting of a copper ion, a manganese ion, a magnesium ion, a zinc ion, a nickel ion, a cobalt ion, an iron ion, an aluminum ion, and a calcium ion.

9. The method of claim 1, wherein the polynucleotide comprises the nucleotide sequence of SEQ ID NO: 2.

* * * * *